United States Patent [19]

Arretz

[11] Patent Number: 5,068,445

[45] Date of Patent: Nov. 26, 1991

[54] PROCESS FOR THE PREPARATION OF ORGANIC DISULPHIDES AND POLYSULPHIDES

[75] Inventor: Emmanuel Arretz, Pau, France

[73] Assignee: Societe Nationale Elf Aquitaine (Production), Courbevoie, France

[21] Appl. No.: 331,878

[22] Filed: Apr. 3, 1989

[30] Foreign Application Priority Data

Apr. 14, 1988 [FR] France .................. 88 04962
Sep. 14, 1988 [FR] France .................. 88 11968

[51] Int. Cl.$^5$ ........................................ C07C 319/22
[52] U.S. Cl. .............................. 568/21; 560/147; 568/22; 568/25; 568/26
[58] Field of Search ............ 568/26, 21, 22, 25; 560/147; 502/159; 208/207

[56] References Cited

U.S. PATENT DOCUMENTS

| | | | |
|---|---|---|---|
| 2,237,625 | 4/1941 | Olin ........................... | 568/26 |
| 2,237,627 | 4/1941 | Olin ........................... | 568/26 |
| 3,022,351 | 2/1962 | Mihn et al. .................. | 568/26 |
| 3,392,201 | 7/1968 | Warner ........................ | 568/26 |
| 3,454,488 | 7/1969 | Lewis et al. ................. | 502/159 |
| 4,113,604 | 9/1978 | Carlson ....................... | 208/206 |
| 4,378,305 | 3/1983 | Carlson ....................... | 502/159 |
| 4,459,205 | 7/1984 | Marty et al. ................. | 208/191 |
| 4,564,709 | 1/1986 | Koyama et al. ............... | 568/26 |
| 4,721,813 | 1/1988 | Mark et al. .................. | 568/22 |

FOREIGN PATENT DOCUMENTS

| | | |
|---|---|---|
| 2938156 | 4/1981 | Fed. Rep. of Germany . |
| 1358398 | 3/1964 | France . |
| 1381265 | 11/1964 | France . |
| 2130985 | 11/1972 | France . |
| 2607496 | 3/1988 | France . |
| 1162334 | 8/1969 | United Kingdom . |

OTHER PUBLICATIONS

E. Reid, Organic Chemistry of Bivalent Sulfur, vol. 1, pp. 118-122 (1958), Chem. Publishing Co. Inc. N.Y.
Chemical Abstracts, vol. 107, No. 5, 1987, p. 657, No. 39367c, Columbus, Ohio, U.S., Kuznetsova et al.

*Primary Examiner*—Mary E. Ceperley
*Attorney, Agent, or Firm*—Morgan & Finnegan

[57] ABSTRACT

The invention relates to the preparation of organic disulphides and polysulphides by the action of sulphur on a mercaptan or on a polysulphide which is lower in sulphur, in the presence of a basic catalyst.

In the process according to the invention, an anion exchange resin is used as catalyst.

17 Claims, No Drawings

PROCESS FOR THE PREPARATION OF ORGANIC DISULPHIDES AND POLYSULPHIDES

FIELD OF THE INVENTION

The present invention relates to the preparation of organic disulphides and polysulphides by the action of sulphur on a mercaptan or on a polysulphide which is lower in sulphur, in the presence of a basic catalyst.

BACKGROUND OF THE INVENTION

Oxidation of mercaptans by sulphur is an important access route to organic disulphides. This direct sulphuration with elimination of hydrogen sulphide in accordance with the reaction: $2\ RSH + S \rightarrow RSSR + H_2S$ is generally carried out in the liquid phase and catalyzed by organic or inorganic basic agents, in particular alkaline bases or amines. When it is carried out with solid sulphur in the presence of an amine, this reaction is essentially carried out discontinuously and is accompanied by the formation of higher polysulphides. See U.S. Pat. No. 2,237,625.

To avoid the use of solid sulphur, it has been proposed in French Patent No. 1,358,398 to bring the mercaptan directly into contact with a solution of sulphur in a solvent. The latter is preferably an organic disulphide and principally the disulphide which it is sought to produce. In this process, in which the solution of sulphur in the disulphide is prepared in advance in a special vat, the amine serves not only to catalyze the oxidation reaction but also to increase the solubility of the sulphur in the disulphide. This obtains solutions which are very concentrated in sulphur.

A great improvement in this synthetic route to organic disulphides was the subject of French Patent No. 2,130,985. It comprises adding to a stirred reactor, sulphur in the liquid state above the liquid reaction phase containing the basic catalyst in solution, for example an amine such as triethylamine. This mode of operation enables organic disulphides to be obtained which are devoid of any other polysulphide. It is possible to carry out a simplified continuous process.

Organic polysulphides $RS_nR$ (n>2), particularly aliphatic, cycloaliphatic or aryl polysulphides, and most particularly dialkyl polysulphides, are products of commercial value for diverse applications, particularly as extreme pressure additives in cutting oils.

Their preparation by reacting elementary sulphur with a mercaptan is known. This reaction:

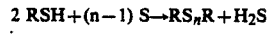
$2\ RSH + (n-1)\ S \rightarrow RS_nR + H_2S$ requires the presence of a basic catalyst which can be an amine, an alkanolamine, an inorganic base, a mercaptide or an alcoholate, or else a catalyst formed by the combination of a mercaptan with an alkylene oxide and an alkaline base. Processes of this kind have been disclosed for example in U.S. Pat. Nos. 2,237,625; 2,237,627; 3,022,351 and 3,392,201 and in French Patent No. 1,381,265; British Patent No. 1,162,334; German Patent No. 2,938,156 and French Patent No. 2,607,496.

The use of magnesium oxide as catalyst has recently been claimed in U.S. Pat. No. 4,564,709. Being solid and insoluble in the liquid reaction media obtained by reacting elementary sulphur with mercaptans or with organic polysulphides, a catalyst of this kind has the advantage of not contaminating the polysulphides produced in these reactions. However, magnesium oxide used in powder form requires very effective filtration of the reaction products, which makes the use of a process of this kind for continuous production of organic polysulphides very sensitive.

The preparation of polysulphides $RS_nR$ can also be carried out by the action of elementary sulphur on organic polysulphides $RS_{n'}R$ having a lower sulphur-rank ($2 \leq n' < n$), for example di-, tri- or tetrasulphides to produce higher polysulphides. This possibility is indicated for example in French Patent No. 1,381,265, amines being present as catalysts.

The preceding references are hereby incorporated by reference.

SUMMARY OF THE INVENTION

It has now been found that, in the preparation of the disulphides $RS_2R$ by action of sulphur on a mercaptan, as well as that of the polysulphides $RS_nR$ by action of sulphur on a mercaptan or a lower polysulphide, anion exchange resins can be used as basic catalysts. These solid resins are generally present in the form of easily separable granules or spheres. Being insoluble in the liquid reaction media, these catalysts can be used in a permanent manner in the reactors, without continuous supplementation, and have the advantage of not contaminating effluents coming out of the reactor.

DETAILED DESCRIPTION OF THE INVENTION

The subject of the invention is a process for the preparation of organic disulphides and polysulphides by the reaction of sulphur on a mercaptan in a liquid medium or on an organic polysulphide which is lower in sulphur, characterized in that an anion exchange resin is used as catalyst.

The present invention is suitable primarily for the preparation of dialkyl disulphides and polysulphides having from 2 to 40 carbon atoms such as dimethyl, diethyl, dipropyl, dibutyl, dipentyl, dihexyl, diheptyl, dioctyl, didecyl or didodecyl disulphides and polysulphides. It is also suitable for the preparation of cycloalkyl disulphides and polysulphides (for example, dicyclohexyl disulphide or polysulphide), arylalkyl disulphides and polysulphides (for example, dibenzyl disulphide or polysulphide) or aromatic disulphides and polysulphides (for example, diphenyl disulphide or polysulphide). The process according to the invention enables also to manufacture functionalized disulphides and polysulphides from mercaptans, the hydrocarbon radical R of which carries one or more functional groups such as, for example, halogen atoms and groups OH, OR', SR', $NH_2$, NHR', NR'R'', CN, CHO, COR', COOH or COOR', wherein R' and R'' denote aliphatic, cycloaliphatic, aromatic or alkylaromatic radicals.

The solid catalysts used according to the invention are organic polymers or copolymers having a basic function, well known in the art as anion exchangers. It is possible to use as such, more particularly resins based on polystyrene crosslinked particularly with divinylbenzene, acrylic resins or phenylacrylic resins, acrylic resins crosslinked with divinylbenzene, or resins of the phenol-formaldehyde type. These resins have tertiary amine or quaternary ammonium functional groups attached by different known techniques, generally after formation of the polymers or copolymers. Epoxy-amine resins obtained by direct reaction of ammonia and epichlorohydrin, the polyvinylpyridines obtained by polymerizing 4-vinylpyridine, and the resins obtained by aminolysis of acrylates with polyamines may also be mentioned. Anion exchange resins are available commercially under different trade names as, for example, Amberlite, Amberlyst, Dowex, Duolite, Lewatit, Reillex, and so on.

Anion exchange resins having quaternary ammonium functional groups are supplied by resin manufacturers in the form of an ionic chloride to guarantee a maximum stability for storage and transport. As their basicity is completely neutralized in this form, these resins must be treated, prior to their being used as catalysts, with a base such as sodium hydroxide to recover their basic properties in the form of quaternary ammonium hydroxide functional groups. In practice the starting resins in chloride form are treated with a suitable solution of sodium hydroxide to eliminate all the chloride ions, then they are washed with water until the sodium hydroxide is completely eliminated.

The effectiveness of anion exchange resins, whether of the amine type or of the quaternary ammonium type (in OH-form) is generally improved when they are used dry. Their catalytic activity is generally observable from a minimum quantity of 0.1% by weight in relation to the sulphur added to the reaction medium. In most cases, the maximum useful quantity is about 50% by weight in relation to the sulphur used, but a larger quantity may prove useful in certain cases, particularly for the preparation of secondary or tertiary dialkyl disulphides and polysulphides. The preferred quantity, however, is generally between 5 and 40% by weight.

The process according to the invention can be carried out in a reactor, provided with a stirrer, in which the catalyst is in suspension in the liquid reaction medium. In this case, any technique for adding sulphur in different forms may be used: sulphur in the solid state, sulphur in the liquid state, a solution of sulphur in a selective solvent, a solution of sulphur in a disulphide or a polysulphide (preferably, that to be produced).

The process according to the invention can also be effected by means of a tubular reactor in which the catalyst is arranged in a fixed bed, a mobile bed or an expanded bed. In this embodiment, the sulphur is introduced either in the liquid state or in solution in the various forms previously mentioned (selective solvent, disulphide or polysulphide).

The actual reaction can take place over a large range of temperatures depending on the mercaptan to be converted and the type of basic resin used. It is generally carried out at a temperature of between −10° C. and the temperature limit of thermal stability of the resin used. Even with the most stable weakly basic resins, it is preferable not to exceed 100° C., particularly in the case of prolonged use of the resin.

The reaction can be carried out at atmospheric pressure. However, in the case of a volatile mercaptan such as methyl mercaptan, it is preferable that the sulphur should be in contact with the liquid mercaptan. The application of a pressure adequate to avoid the entrainment of the mercaptan with the hydrogen sulphide formed can thus favor the reaction. For slightly volatile mercaptans, having a high boiling point, it may be advisable to introduce an inert gas (for example nitrogen) through the reaction mixture or to keep a sufficiently reduced pressure inside the reactor to promote the elimination of hydrogen sulphide as it is formed and thus favor the reaction to the maximum.

The mole ratio mercaptan/sulphur to be used may be in the range from 0.3 to 6 and is selected according to the nature of the mercaptan used and of the product (disulphide or polysulphide) to be prepared.

To prepare a disulphide in accordance with the reaction:

$$2\ RSH + S \rightarrow R\text{-}SS\text{-}R + H_2S$$

the molar ratio mercaptan/sulphur must be at least equal to 2. However, to obtain an excellent selectivity to disulphide and so reduce to the minimum the concomitant formation of polysulphides, it is generally suitable to operate with an excess of mercaptan with respect to the stoechiometry, the molar ratio mercaptan/sulphur being preferably between 3 and 5.

The reaction of formation of the polysulphides ($n \geq 3$) being:

$$2\ R\text{-}SH + (n-1)S \rightarrow R\text{-}S_n\text{-}R + H_2S$$

the sulphur rank (n) of the polysulphide obtained varies in inverse proportion to the molar ratio mercaptan/sulphur used. For primary or secondary mercaptans, it is advantageous to operate with a low molar ratio (at most equal to 1 and, preferably, lower than 1) to avoid retrogradation of the polysulphides to the disulphide. By contrast, for tertiary mercaptans such as, for example, tertiobutylmercaptan or tertio-octylmercaptan, the molar ratio mercaptan/sulphur may be up to 3 without inconvenience.

Where the starting material is an organic polysulphide (for example di-, tri-, tetrasulphide and so on), the quantity of sulphur to be used is determined as a function of this starting polysulphide and of the polysulphide, higher in sulphur, which is to be synthesized. The mole ratio between the two reactants: organic polysulphide starting material and sulphur may vary from 0.2 to 1.

EXAMPLES

The following examples illustrate the invention without limiting it.

EXAMPLE 1: DIMETHYL DISULPHIDE

The reactor used is provided with a central stirrer and a double outer shell. It is equipped for working either at atmospheric pressure or under pressure. The useful reaction volume is about 300 ml.

First Trial 94 g of dimethyl disulphide and 32 g of solid sulphur are introduced into the reactor. 5 g of anionic resin having tertiary amine functional groups (Amberlyst A 21 produced by Rohm and Haas), previously dried, is subsequently added with stirring. After the sulphur dissolves, gaseous methyl mercaptan is injected into the stirred liquid medium by means of a downpipe, with an output of 24 l/h for 2 hours (which is about 2 mol in total). The temperature of the reaction is maintained at 30° C. After separation of the resin, the reaction liquid is treated with a current of nitrogen to eliminate the unused methyl mercaptan and the hydrogen sulphide formed which remains dissolved. The production of dimethyl disulphide, namely 31 g, is determined by weighing and analysis of the liquid mixture recovered. This is a yield of 32% in relation to the sulphur added.

Second Trial

In the same reactor cooled to −10° C., 192 g of methyl mercaptan, added in gaseous form, are condensed. Successive additions are made to the liquid methyl mercaptan of 32 g of solid sulphur, and 5 g of Amberlyst A 21 resin. An evolution of gas formed from hydrogen sulphide and from entrained methyl mercaptan is quickly observed. The mixture is kept at a temperature of −10° C. while stirring. After 1 hour, the resin is separated from the reaction mixture. After elimination of the remaining methyl mercaptan and of the dissolved hydrogen sulphide using a current of nitrogen, 85 g of a liquid are obtained. The analysis of which shows that it is composed of 95% dimethyl disulphide. The remainder comprises organic polysulphides. The yield of dimethyl disulphide is 85.9% in relation to the sulphur added.

Third Trial

In the same reactor, 32 g of solid sulphur and 5 g of Amberlyst A 21 anionic resin are added. Then the reactor is pressurized with nitrogen to a pressure of 3 bars absolute. Subsequently, 192 g of liquid methyl mercaptan are added. The reaction medium is kept at a temperature of 30° C., with stirring and at a pressure of 3 bars absolute by means of a pneumatic pressure reducing valve whose outlet to atmospheric pressure enables gaseous products from the reaction to be eliminated. After 1 hour, the crude reaction product is recovered separately from the resin. The methyl mercaptan and the dissolved hydrogen sulphide are eliminated. 90 g of a liquid are obtained. The analysis of which shows that it is composed of 95.2% dimethyl disulphide. The remainder comprises polysulphides. The yield of dimethyl disulphide is 91.1% in relation to the sulphur added.

Fourth Trial

The reactor initially containing 5 g of Amberlyst A 21 resin is charged under a pressure of 3 bars absolute of nitrogen with 192 g of liquid methyl mercaptan. By means of an appropriate injection system, 32 g of liquid sulphur are subsequently added with stirring over a period of 20 minutes. The reactor is kept at a temperature of 40° C. and at a pressure of 3 bars absolute. The gaseous effluents are eliminated continuously to atmospheric pressure by the pressure relief valve. After 10 minutes, the reaction product is recovered separately from the resin and is treated with a current of nitrogen to eliminate methyl mercaptan and dissolved hydrogen sulphide. 92 g of liquid are obtained. The analysis of which shows that it is composed of 97% dimethyl disulphide. The remainder comprises polysulphides. The yield of dimethyl disulphide is 94.9% in relation to the sulphur added.

EXAMPLE 2: DIETHYL DISULPHIDE

In the same reactor as in Example 1, 186 g of ethyl mercaptan, 24 g of sulphur and 4 g of anhydrous Amberlyst A 21 resin are added. The mixture is subsequently stirred for 1 hour, at a temperature of 30° C. After separation from the resin, a liquid is obtained. The analysis of which shows that it contains 87 g of diethyl disulphide, which represents a yield of diethyl disulphide of 95% in relation to the sulphur added.

This operation is repeated with other anion exchange resins under identical conditions (the same quantities of ethyl mercaptan, sulphur and resin; temperature: 30° C.).

The products IRA-400 and A-26 are resins having quaternary ammonium functional groups. The products IRA-94 S and IRA-93 SP are resins having tertiary amine functional groups.

The results obtained are presented in the following table:

| RESIN | REACTION TIME (HOUR) | YIELD (%) OF DI-ETHYL DISULPHIDE |
|---|---|---|
| A-21 | 1 | 95 |
| IRA-400 | 1 | 40 |
|  | 3 | 90 |
| A-26 | 1 | 97 |
| IRA-94 S | 1 | 98 |
| IRA-93 SP | 1 | 98.5 |

EXAMPLE 3: DI(N-PROPYL) DISULPHIDE

Operation is as described in Example 2, but the ethyl mercaptan is replaced by 228 g of n-propyl mercaptan. The yield of di(n-propyl) disulphide is 93% in relation to the sulphur added.

EXAMPLE 4: DI(N-DODECYL) DISULPHIDE

The same reactor as in Example 1 is charged with 202 g of n-dodecyl mercaptan, 8 g of sulphur and 3 g of Amberlyst A 21 resin. At ambient temperature, formation of the disulphide is slow. On the other hand, when the temperature is increased, a strong evolution of hydrogen sulphide is observed. After having kept the reaction medium at 75° C. for 1 hour, a liquid is recovered. The analysis of which shows that it contains essentially dodecyl disulphide and the excess of n-dodecyl mercaptan. The yield of di(n-dodecyl) disulphide is 98% in relation to the sulphur added.

EXAMPLE 5: DIPHENYL DISULPHIDE

To the same reactor, 220 g of thiophenol, 16 g of sulphur and 4 g of Amberlyst A 21 resin are added. The mixture is kept at ambient temperature while stirring. At the end of the evolution of hydrogen sulphide, the liquid is recovered. The analysis of which shows that it is wholly composed of diphenyl disulphide and excess thiophenol. The yield of diphenyl disulphide is 99% in relation to the sulphur added.

EXAMPLE 6: DI-ISOPROPYL DISULPHIDE

The same reactor as in Example 1 is charged with 190 g of isopropyl mercaptan, 20 g of sulphur and 3 g of Amberlyst A 21 resin. At ambient temperature, the formation of the disulphide represents about 40% of the theoretical proportion. The reactor is then slightly pressurized with nitrogen (0.4 bar absolute). The reaction medium is heated and kept stirred at a temperature of 60° C. for 1 hour. The crude product of the reaction is subsequently analyzed. Di-isopropyl disulphide is obtained with a yield of 93%.

EXAMPLE 7: BIS(2-HYDROXYETHYL) DISULPHIDE

The same reactor as in example 1 is charged with 195 g of mercaptoethanol, 20 g of solid sulphur and 7.6 g of anhydrous Amberlyst A 21 resin. The mixture is then stirred for one hour at ambient temperature, then heated at 85° C. for half an hour. After separation of the resin, a liquid is obtained. The analysis of which shows that is contains essentially bis(hydroxyethyl) disulphide and the excess of mercaptoethanol. The yield of this disulphide is 97.5% in relation to the sulphur added.

EXAMPLE 8: METHYL 3,3'-DITHIODIPROPIONATE

The same reactor as in example 1 is charged with 240 g of methyl 3-mercaptopropionate, 16 g of solid sulphur and 7 g of anhydrous Amberlyst A 21 resin. The mixture is stirred for one hour at ambient temperature. Then it is heated at 85° C. for one hour and a half. The disuphide $(CH_3O—CO—CH_2CH_2)_2S_2$ is thus obtained with a yield of 96% in relation to the sulphur added.

EXAMPLE 9: DIMETHYL POLYSULPHIDE FROM METHYL MERCAPTAN

The reactor is as in example 1, but its useful reaction volume is of the order of 600 ml. 64 g of solid sulphur and 6 g of dry Amberlyst A 21 resin (anionic resin with tertiary amine functional groups produced by Rohm and Haas), are added to the reactor. Then the reactor is pressurized with nitrogen up to a pressure of 3 bars absolute. 48 g of liquid methyl mercaptan is subsequently added. The reaction mixture is kept at 30° C. with stirring and at a pressure of 3 bar absolute by means of a pneumatic pressure relief valve whose outlet to atmospheric pressure enables the gaseous products of the reaction to be eliminated. After one hour, the resin is separated from the crude reaction product which is treated with a current of nitrogen to eliminate the unused methyl mercaptan and dissolved hydrogen sulphide.

85 g of a liquid is thus obtained. The analysis of which shows that it is composed of a mixture of polysulphides having the following distribution by weight:
dimethyl disulphide 1.5%
dimethyl trisulphide 27.7%
dimethyl tetrasulphide 30.9%
dimethyl pentasulphide 24.3%
higher polysulphides 15.6%

EXAMPLE 10: DIMETHYL POLYSULPHIDE FROM DIMETHYL DISULPHIDE 64 g of solid sulphur, 8 g of Amberlyst A 21 resin and 94 g of dimethyl disulphide are added to the same reactor as in example g. Then the mixture is kept at 60° C. at atmospheric pressure with stirring for 2 hours.

After separation of the resin and elimination of the dissolved gas, 152 g of a liquid is recovered. The analysis of which shows the following composition by weight:
dimethyl disulphide 2.1%
dimethyl trisulphide 47.2%
dimethyl tetrasulphide 31.4%
dimethyl pentasulphide 18.1%
higher polysulphides 1.2%

EXAMPLE 11: DI-TERT-BUTYL POLYSULPHIDE FROM TERT-BUTYL MERCAPTAN

A series of three trials is carried out using 52 g of sulphur, 10 g of dry Amberlyst A 21 resin and a variable quantity (440 g, 293 g or 73.3 g) of tert-butyl mercaptan (TBM). Each trial is carried out at 60° C. at atmospheric pressure with stirring for a period of 3 hours.

The results obtained are presented in the following table:

| MOLE RATIO $\frac{TBM}{S}$ | DISTRIBUTION OF DI-TERT-BUTYL POLYSULPHIDES $C_4H_9—S_n—C_4H_9$ (% BY WEIGHT) | | | | |
|---|---|---|---|---|---|
| | n = 2 | n = 3 | n = 4 | n = 5 | n > 5 |
| $\frac{3}{1}$ | 4.1 | 59.3 | 30.7 | 5.9 | — |
| $\frac{2}{1}$ | 1.1 | 27.8 | 61.5 | 9.2 | 0.4 |
| $\frac{1}{2}$ | — | 10.8 | 72.1 | 16.1 | 1 |

A series of three trials carried out under the same conditions, but replacing Amberlyst A 21 resin with Amberlite IRA 93 SP (anionic resin with tertiary amine functional groups) gave practically equivalent results.

EXAMPLE 12: DI-TERT-OCTYL POLYSULPHIDE FROM TERT-OCTYL MERCAPTAN

Three trials are carried out each at 80° C. at atmospheric pressure with stirring for 3 hours, using 32 g of sulphur, 10 g of dry Amberlyst A 21 resin and a variable quantity (439 g, 292.6 g or 73.2 g) of tert-octyl mercaptan (TOM).

The following table presents the results obtained:

| MOLE RATIO $\frac{TOM}{S}$ | DISTRIBUTION OF DI-TERT-OCTYL POLYSULPHIDES $C_8H_{17}—S_n—C_8H_{17}$ (MOL % DETERMINED BY NMR) | | | | |
|---|---|---|---|---|---|
| | n = 3 | n = 4 | n = 5 | n = 6 | n > 6 |
| $\frac{3}{1}$ | 44 | 56 | — | — | — |
| $\frac{2}{1}$ | 34 | 66 | — | — | — |
| $\frac{1}{2}$ | 7 | 48 | 20 | 11 | 14 |

EXAMPLE 13: DI-TERT-NONYL POLYSULPHIDE FROM TERT-NONYL MERCAPTAN 32 g of solid sulphur, 5 g of dry Amberlyst A 21 resin and 80 g of tert-nonyl mercaptan, obtained from a propylene trimer, are added to the same reactor as in example g. The mixture is subsequently kept at 80° C. at atmospheric pressure for 3 hours with stirring.

After separation of the resin and degassing of the liquid with a current of nitrogen, a di-tert-nonyl polysulphide is obtained whose sulphur content is 37.9%, which corresponds to a yield of 98.2% of the theoretical yield.

EXAMPLE 14: DI-TERT-DODECYL POLYSULPHIDE FROM TERT-DODECYL MERCAPTAN

The operation is carried out as in Example 13, but replacing the tert-nonyl mercaptan with 101 g of tert-dodecyl mercaptan obtained from a propylene tetramer.

The sulphur content of the di-tert-dodecyl polysulphide thus obtained is 31.3%, which corresponds to a yield of 97.4% of the theoretical yield.

EXAMPLE 15: BIS(2-HYDROXYETHYL) POLYSULPHIDE

The reactor is charged with 46.8 g of mercaptoethanol, 19.2 g of solid sulphur and 2 g of dry Amberlyst A 21 resin. The mixture is subsequently stirred for one hour at ambient temperature, then for one hour at 85° C.

After separation of the resin and degassing, a liquid is obtained, the analysis of which shows the following molar composition:
bis(hydroxyethyl) disulphide 12%
bis(hydroxyethyl) trisulphide : 51%
bis(hydroxyethyl) higher polysulphides: 37%

EXAMPLE 16: METHYL 3,3'-POLYTHIODIPROPIONATE

It is operated as in example 15, except that mercaptoethanol is replaced by 72 g of methyl 3-mercaptopropionate and the time of heating at 85° C. is an hour and a half.

Analysis of the liquid thus obtained shows that it consists of a mixture of polysulphides of formula:

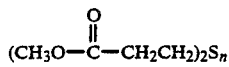

$$(CH_3O-\overset{\overset{O}{\|}}{C}-CH_2CH_2)_2S_n$$

in the following molar proportions:

| n | % |
|---|---|
| 2 | 15 |
| 3 | 47 |
| ≧4 | 38 |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the intended spirit and scope of the appended claims.

I claim:

1. A process for the preparation of organic disulphides and polysulphides comprising reacting sulphur with a mercaptan or a polysulphide which is lower in sulphur, in a liquid medium in the presence of a basic catalyst, said catalyst being an anion exchange resin consisting essentially of an organic polymer or copolymer having a basic function.

2. The process according to claim 1, wherein the quantity of resin used is between 0.1% and 50% by weight in relation to the sulphur added.

3. The process according to claim 2, wherein the quantity of resin used is between 5% and 40% by weight of the sulphur added.

4. The process according to claim 1, wherein the reaction is carried out at a temperature between −10° C. and the temperature limit of thermal stability of the resin used.

5. The process according to claim 4, wherein the temperature is below 100° C.

6. The process according to claim 1, wherein the anion exchange resin is a resin having tertiary amine functional groups or quaternary ammonium functional groups.

7. The process according to claim 1, wherein the mercaptan is an alkyl mercaptan, cycloalkyl mercaptan, aryl mercaptan or aralkyl mercaptan.

8. The process according to claim 7, wherein the hydrocarbon radical of the mercaptan carries one or more functional groups.

9. The process according to claim 1, wherein the molar ratio mercaptan/sulphur is between 0.3 and 6.

10. The process according to claim 1 for preparing disulphides, wherein the molar ratio mercaptan/sulphur is between 2 and 6.

11. The process according to claim 10, wherein the molar ratio mercaptan/sulphur is between 3 an 5.

12. The process according to claim 1 for preparing polysulphides from primary or secondary mercaptans, wherein the molar ratio mercaptan/sulphur is between 0.3 and 1.

13. The process according to claim 1 for preparing polysulphides from tertiary mercaptans, wherein the molar ratio mercaptan/sulphur is between 0.3 and 3.

14. The process according to claim 1 for preparing polysulphides $RS_nR$ from polysulphides $RS_{n'}R$ ($2 \leq n' < n$), wherein the molar ratio of the polysulphide $RS_{n'}R$ to sulphur added is between 0.2 and 1.

15. The process according to claim 1, wherein the catalyst is a resin having tertiary amine or quaternary ammonium hydroxide function groups.

16. The process according to claim 15, wherein the catalyst is a resin based on polystyrene crosslinked with divinylbenzene, acrylic resins or phenylacrylic resins, acrylic resins crosslinked with divinylbenzene or resins of phenol-formaldehyde.

17. The process according to claim 1, wherein the catalyst is an epoxy-amine resin obtained by direct reaction of ammonia and epi-chlorohydrin, a polyvinylpyridine obtained by polymerizing 4-vinylpyridine or resins obtained by aminolysis of acrylates with polyamines.

* * * * *